United States Patent
Viñas et al.

(10) Patent No.: US 7,906,495 B2
(45) Date of Patent: Mar. 15, 2011

(54) MONOHALOGENOVINYL VITAMIN D DERIVATIVE COMPOUNDS

(75) Inventors: Antonio Buxadé Viñas, Barcelona (ES); Antonio Conchillo Teruel, Barcelona (ES); Carlos Mola Soler, Barcelona (ES)

(73) Assignee: Laboratorios Vinas S.A., Barcelona (ES)

( * ) Notice: Subject to any disclaimer, the term of this patent is extended or adjusted under 35 U.S.C. 154(b) by 946 days.

(21) Appl. No.: 10/579,594

(22) PCT Filed: Nov. 17, 2004

(86) PCT No.: PCT/ES2004/000511
§ 371 (c)(1),
(2), (4) Date: May 17, 2006

(87) PCT Pub. No.: WO2005/051903
PCT Pub. Date: Jun. 9, 2005

(65) Prior Publication Data
US 2007/0129558 A1 Jun. 7, 2007

(30) Foreign Application Priority Data

Nov. 28, 2003 (ES) .................................. 200302806

(51) Int. Cl.
*A61K 31/59* (2006.01)
*C07C 401/00* (2006.01)

(52) U.S. Cl. ........................................ 514/167; 552/653
(58) Field of Classification Search ................... 514/167; 552/653; 568/816, 817
See application file for complete search history.

(56) References Cited

U.S. PATENT DOCUMENTS 4,847,012 A * 7/1989 DeLuca et al. ................ 552/653

FOREIGN PATENT DOCUMENTS

| EP | 78704 A | 5/1983 |
|---|---|---|
| WO | WO 9203414 A | 3/1992 |
| WO | WO 2004037781 | 5/2004 |

OTHER PUBLICATIONS

Database CA in STN, AN 106:83937 & Takai et al., J. American Chemical Society, vol. 108, n° 23, pp. 7408-7410, 1986. "Simple and selective method for aldehydes, conversion by means of a haloform-cormous chloride system". Abstract.

* cited by examiner

*Primary Examiner* — Taylor Victor Oh
(74) *Attorney, Agent, or Firm* — Wood, Phillips, Katz, Clark & Mortimer

(57) ABSTRACT

New vitamin D derivative compounds containing a monohalovinyl moiety at position C-20 are described.

A process for obtaining the new compounds, consisting of reacting an aldehyde precursor with a haloform in the presence of $Cr^{2+}$ salts, is also described.

21 Claims, No Drawings

MONOHALOGENOVINYL VITAMIN D DERIVATIVE COMPOUNDS

FIELD OF THE INVENTION

The present invention relates to new (C20)-monohalogenovinyl derivative compounds of formula (I)

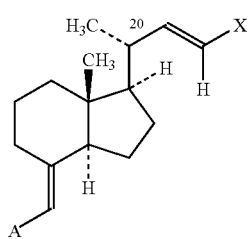

(I)

and to a process for obtaining said compounds.

BACKGROUND OF THE INVENTION

Intermediate vitamin D derivatives with reactive groups at C-20 are widely used in synthesizing vitamin D derivatives with use, or potential use, in different therapeutic fields, for example: bone metabolism diseases, diseases characterized by altered cell differentiation and proliferation (dermatology and oncology), etc.

The chemistry of both closed and open cycle system steroids is complex due to the simultaneous combination in the molecules of different functionalization and several chiral centers, therefore there is a special interest in reactions and reactants that allow greater selectivity and specificity in the reaction products.

European patent application EP78704-A1 discloses intermediates for the synthesis of vitamin D derivatives with general formulas:

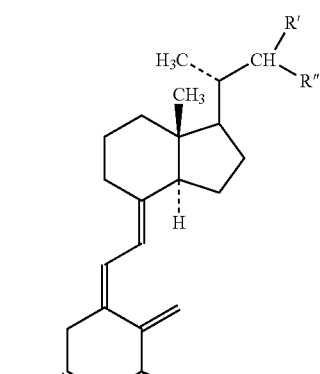

(II)

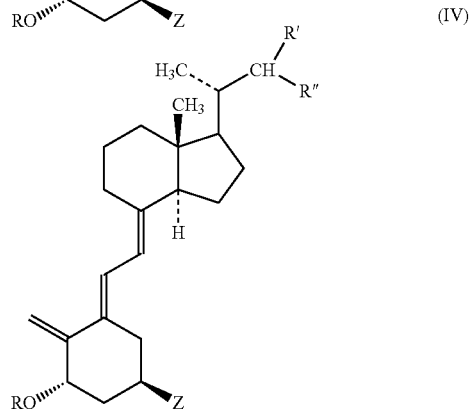

(III)

(IV)

Wherein, among many other possibilities, R' and R" may represent an optionally substituted alkylidene group. However, said patent application does not disclose a single specific case of a compound in which said positions configure a double bond substituted with a single halogen atom. Furthermore, the aforementioned intermediates are prepared by means of a Wittig reaction on the aldehyde precursor.

Patent application WO92/03414-A discloses the compound 1(S),3(R)-bis-tert-butyldimethylsilyloxy)-20(R)-(2,2-dichlorovinyl)-9,10-seco-pregna-5(E),7(E),10(19)-triene as an intermediate for obtaining vitamin D analogues having at least one triple bond in the side chain at C-20 (the corresponding dibrominated derivative is also claimed), and the article by Calverley et al. (*Bioorganic Medicinal Chemistry Letters*), Vol. 3, No. 9, pp. 1841-1844 (1993) discloses the compound of formula (V) (corresponding 20(S) isomer) for the same purpose as the alkyne precursor.

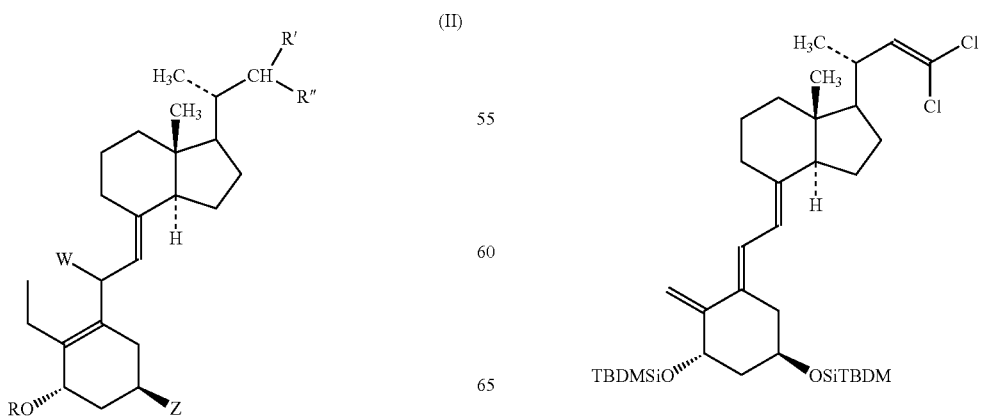

(V)

Although structurally similar to the monohalogen derivatives object of this invention, these dihalogenated compounds are actually different in their structure, in their synthesis and in their reactivity, since from dihalogenated compounds it is very difficult to obtain halogen-free alkenes in a single step, which can be easily obtained from monohalogenated compounds. Nor have mono- or diiodoalkenyl derivatives been disclosed, which are considered to be more interesting due to the greater reactivity of iodine.

The authors of the present invention have found that new useful compounds having a monohalovinyl group as a side chain joined at C-20 allow a new synthesis route that is able to provide pharmacologically useful vitamin D derivatives with better efficiencies and greater stereoselectivity, methodological simplicity and fewer byproducts and impurities. For example, these alkenyl monohalo derivatives are susceptible to being used for preparing a wide variety of organometallic compounds by substitution of the halogen with a metal, which are satisfactorily used to form new C—C bonds.

Therefore, the object of the present invention are new compounds useful for obtaining vitamin D derivatives having a monohalovinyl group as a side chain joined at C-20.

A process for preparing said compounds further belongs to the object of the present invention.

DETAILED DESCRIPTION OF THE INVENTION

The new compounds correspond to general formula (I)

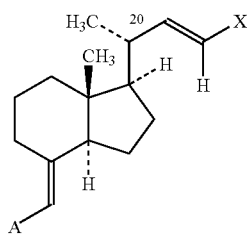

(I)

wherein:
X is an halogen atom selected from chlorine, bromine and iodine and
A is selected from any of the moieties corresponding to general formulas (A1), (A2) and (A3)

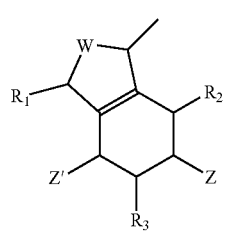

(A1)

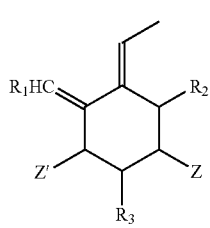

(A2)

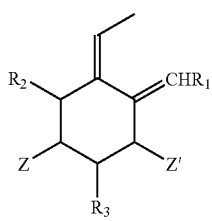

(A3)

wherein:

Z and Z' are selected independently from hydrogen, a hydroxyl group and an —OR protected hydroxyl group, where R is a hydroxyl protective group; in a particular embodiment, R is any of the hydroxyl protective groups of those described in Green T W et al. "Protective groups in Organic Synthesis", Third Edition (1999), Ed. John Wiley & Sons (ISBN 0-471-16019-9);

W represents a dienophile selected from $SO_2$ and a diacylazo compound such as 4-phenyl-1,2,4-triazolin-3,5-dione or phthalazin-1,4-dione; and $R_1$, $R_2$ and $R_3$ are independently selected from hydrogen, halogen, a hydroxyl group, eventually protected with a hydroxyl protective group, such as any of the previously mentioned hydroxyl protective groups, $C_1$-$C_6$ alkyl or $C_1$-$C_6$ alkenyl, optionally substituted with halogen, hydroxyl, cyano or amino, or a dialkyl($C_1$-$C_5$)ether or alkyl($C_1$-$C_5$)amino group.

As it is used in this description, the term "alkyl" refers to a radical derivative of a linear or branched chain saturated hydrocarbon. Similarly, the term "alkenyl" refers to a radical derivative of a linear or branched chain unsaturated hydrocarbon.

Preferably X is an iodine atom and, independently, it is also preferred that W be the $SO_2$ group.

Also preferred are the compounds in which $R_1$, $R_2$ and $R_3$ are independently selected from hydrogen, halogen and hydroxyl, being particularly preferred the case in which $R_1$, $R_2$ and $R_3$ are simultaneously hydrogen.

Also preferred are the compounds in which Z and Z' are independently selected from a hydroxyl group and an RO-protected hydroxyl group in which the protective group is selected from silyl ethers and carboxylic esters disclosed in the previously mentioned book of Green TW et al.

Particularly preferred are the compounds in which simultaneously:

X is an iodine atom,
W is the $SO_2$ group
$R_1$, $R_2$ and $R_3$ are hydrogen,

Z and Z' are independently selected from a hydroxyl group and an —OR protected hydroxyl group in which the protective group is selected from the silyl ethers and carboxylic esters disclosed in the previously mentioned book of Green TW et al, and particularly those corresponding to the following formulas (IA1), (IA2) and (IA3):

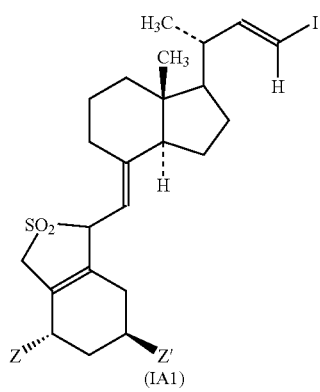

(IA1)

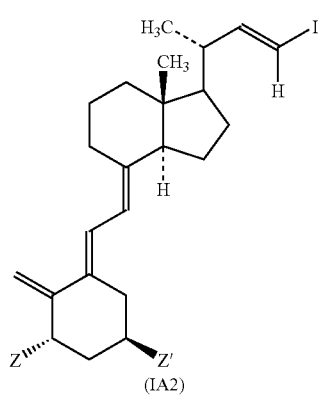

(IA2)

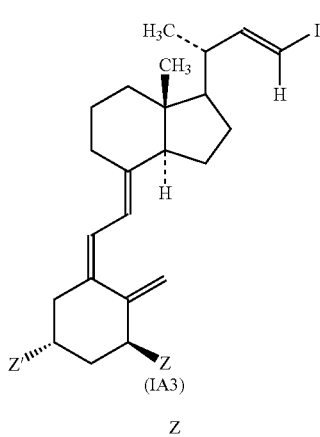

(IA3)

| | Z | Z' |
|---|---|---|
| IA1a/IA2a/IA3a | TBDMSiO | TBDMSiO |
| IA1b/IA2b/IA3b | AcO | AcO |
| IA1c/IA2c/IA3c | HO | HO | wherein TBDMS and Ac represent the universally accepted abbreviations for, respectively, the tert-butyldimethylsilyl group and the acetyl group.

Compounds of formula (I) can be obtained by means of reaction of an aldehyde of general formula (VI)

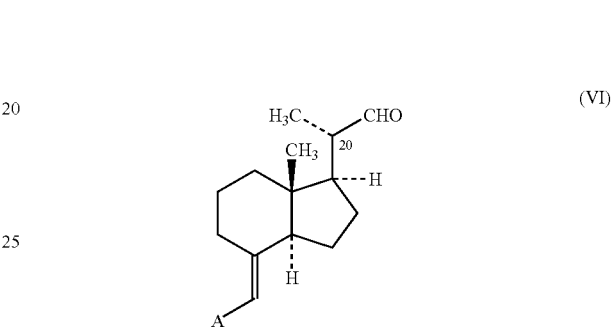

(VI)

in which A has the aforementioned meaning, with a haloform selected from chloroform, bromoform and iodoform, in the presence of a divalent chromium ($Cr^{2+}$) salt or complex, and if so desired, converting the compound of formula (I) into another desired compound of formula (I).

Should the starting aldehyde have a moiety A that is different from what is finally desired to be obtained, the process is complemented in the following manner:

when moiety A in the starting aldehyde (VI) corresponds to general formula (A1) and the compound of formula (I) is wished to be obtained, in which A is the moiety of general formula (A2), the product obtained from the reaction of the aldehyde with the haloform in the presence of a $Cr^{2+}$ complex or salt is reacted with a base, when moiety A in the starting aldehyde (VI) corresponds to general formula (A1) and the compound of formula (I) is wished to be obtained, in which A is the moiety of general formula (A3), the product obtained from the reaction of the aldehyde with the haloform in the presence of a $Cr^{2+}$ complex or salt is first reacted with a base and then subjected to UV or VIS light irradiation until obtaining the 5(Z) configuration, and when moiety A in the starting aldehyde (VI) corresponds to general formula (A2) and the compound of formula (I) is wished to be obtained, in which A is the moiety of general formula (A3), the product obtained from the reaction of the aldehyde with the haloform in the presence of a $Cr^{2+}$ complex or salt is subjected to UV or VIS light irradiation until obtaining the 5(Z) configuration, all this is represented in the following scheme:

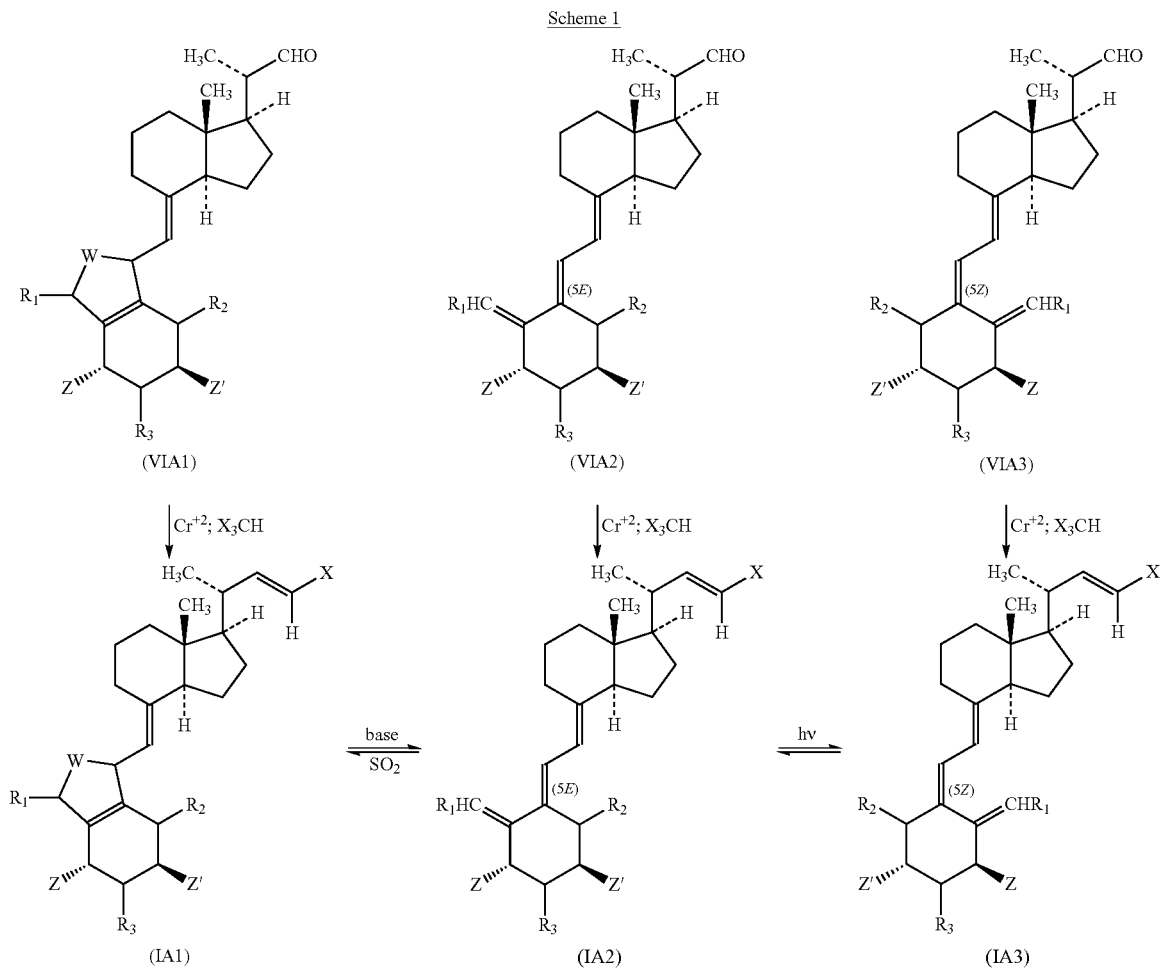

Although the reaction of aldehydes with metal ions of the $Cr^{2+}$ type was already known, it had not been applied to date to steroidal compounds, and the authors of the present invention have surprisingly found that said reaction applied to aldehydes of formula (VI) allows obtaining halovinyl derivatives of formula (I) with a high efficiency and a stereoselectivity for the trans form between C-22 and C-23 that can reach up to 98% in the case of the iodovinyl derivatives, whereas the classic methods based on the Wittig reaction using $Ph_3P=CHX$ (JACS, 108, 7408, 1986) as a reactant provide lower efficiencies and a much lower degree of stereoselectivity. Other known methods, such as the addition of metal/iodine hydrides to alkynes obtained from aldehydes, are more complex and though they show a good stereoselectivity, the latter is not always aimed at obtaining the trans form between C-22 and C-23.

The starting aldehydes of formula (VI) are known and can be obtained by means of the methods disclosed, for example, in European patent application EP78704-A1, in Calverley MJ, *Tetrahedron* Vol. 43, No. 20, pp. 4609-4619 (1987), in DeLuca et al. *Tetrahedron Letters*, Vol. 28, No. 49, pp. 6129-6132 (1987) and in DeLuca et al. *J. Org. Chem.* 1988, 53, 3450-3457.

The reaction of the aldehydes of formula (VI) with the haloform in the presence of divalent chromium salts can be carried out in a polar aprotic solvent, preferably of the ether type and more preferably in tetrahydrofuran (THF), at a temperature comprised between −50° C. and +30° C.

The preferred divalent chromium salt is the $Cr^{2+}$ chloride ($CrCl_2$), although it is also possible to use a salt obtained in situ from a trivalent chromium salt by means of reduction thereof with: a metal hydride, such as, for example, lithium and aluminum hydride ($LiAlH_4$); tetrakis(dimethylaminoethylene); electroreduction; and metal manganese—the latter in the presence of chlorotrimethylsilane—or else using chromium chloride ($CrCl_2$) in small amounts which are regenerated with the Mn/chlorotrimethylsilane system.

The compounds of formula (I) in which A is the moiety of general formula (A2) can also be obtained from the compounds of formula (I) in which A is the moiety of general formula (A1), by means of removal of dienophile W by treating with a base when the former is $SO_2$. Inversely, the compounds of general formula (IA1) can also be obtained from (IA2) and (IA3) by reaction with liquid $SO_2$ at −10° C.

In turn, the compounds of formula (I) in which A is the moiety of general formula (A3), with the 5(Z) configuration, can also be obtained from the compounds of formula (I) in which A is the moiety of general formula (A2), having the 5(E) configuration, by means of light irradiation. Irradiation can be carried out in the presence of iodine or diphenyl selenide and diffuse light, or else in the presence of photosensitizers derived from anthracene, acridine or phenazine and ultraviolet light. In all these cases, cis/trans mixtures in different proportions are obtained.

The compounds of formula (I) in which Z and/or Z' are (—OR) protected hydroxyl groups can be converted into free hydroxyl groups by means of any of the deprotection techniques that are well known by the person skilled in the art, for example those disclosed in the aforementioned book of Green TW. Said free hydroxyl groups can in turn be protected again or acylated, if so desired, by means of conventional techniques that are well known by the person skilled in the art, none of this affecting the halovinyl group joined at C-20.

The preferred synthesis route is the one that starts from (VIA1) and efficiencies (IA1) and then (IA2) or (IA3). In obtaining aldehydes (VIA2) and (VIA3), a certain racemization always occurs in the C-20 carbon. In the aforementioned route, one of the objectives of this invention, racemization at C-20 does not occur in any step, which constitutes an advantage since no costly purification steps have to be carried out. When new compounds are obtained from aldehydes (VIA2) or (VIA3), usually raw aldehydes are used, but purification must be carried out later in the reaction products obtained with these aldehydes. In contrast, purification processes will be unnecessary when the compounds are prepared from the iodine derivatives obtained and described in this invention, given that in the process for obtaining said iodine derivatives no racemization at C-20 occurs and, therefore, stereochemically pure iodine derivatives are provided as a starting point.

As a further advantage, it is worth mentioning, as previously indicated, that the double halogenovinyl bond that is formed is trans, compared to other methods which give cis/trans mixtures in a greater or lesser proportion.

In another aspect, the invention is related to the use of said compounds of general formula (VI) for obtaining a compound of general formula (I).

EXAMPLES

The nuclear magnetic resonance (NMR, δ) spectra were performed at 300 and 200 MHz in a $CDCl_3$ solution using internal standard TMS or $CHCl_3$. The coupling constants J are given in Hertz (s=singlet, d=doublet, t=triplet, dd=double doublet, AB=AB system, m=multiplet and w.b.=wide band or sum of several signals).

The infrared (IR) spectra were performed by means of KBr pellets and only the most intense or characteristic frequencies are given in $cm^{-1}$.

Analytical high pressure liquid chromatography (HPLC) was performed with a normal phase column: Hypersil, 5 micron, 4.6×100 mm and mixtures of hexane and dichloroethane or ethyl acetate as eluents depending on the type of compound to be eluted and analyzed. Preparative high performance liquid chromatography was performed in a Microporasil column, 10×250 mm or in PrePac Waters with silica gel cartridges 40×100 mm. Thin layer chromatography (TLC) was performed with Merck 60 F254 Silica Gel plates. Preparative flash chromatography was performed with Silica Gel 60 A and 35-70 microns and at a pressure of 0.75-1.0 atmospheres.

Photochemical reactions with ultraviolet light were performed with a Heraeus TQ 500 Z2 lamp.

The solutions were dried on anhydrous sodium sulfate containing 5% anhydrous $Na_2SO_4$ and 5% anhydrous $K_2CO_3$; they were filtered and concentrated in a rotary evaporator.

DMAP means: dimethylaminopyridine.
MTBE means: methyl t-butyl ether.
TBDMS: tert-butyldimethylsilyl.

The reactions were always carried out with the greatest possible absence of light in order to prevent cis/trans isomerizations.

All the reactions were carried out in nitrogen atmosphere, being necessary to completely exclude the presence of $O_2$ and $H_2O$ in the reactions in which $Cr^{+2}$ is involved, even being necessary to weigh the reactant in nitrogen atmosphere.

Example 1

Preparation of the Compound of Formula (IA1a)

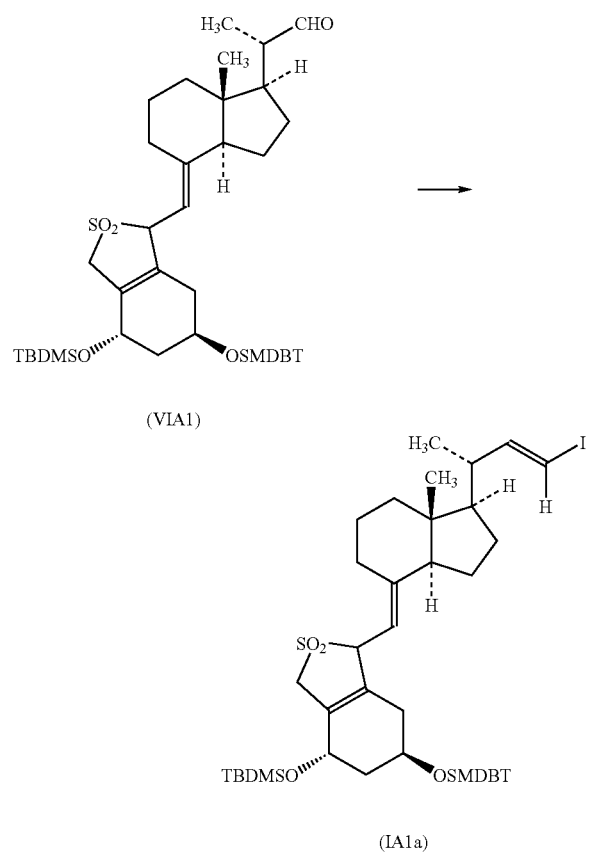

(VIA1)

(IA1a)

($R_1, R_3$ = H; Y = $SO_2$; Z, Z' = TBDMSO⁻)

A solution of 2.37 g of aldehyde (VIA1) and 2.92 g of $I_3CH$ in 15 ml of THF is added to a reactor containing 3.0 g of $CrCl_2$ and 15 ml of THF by means of a cannula and $N_2$ pressure with a thorough exclusion of oxygen and moisture. Pressure is controlled so that the rate of addition is such that the temperature remains between −5 and +5° C. Once the addition has ended, this temperature is maintained until a control by means of TLC indicates the virtual disappearance of aldehyde (usually 2-3 hours). Then 40 ml of hexane and 40 ml of brine are added, it is stirred for 20 minutes and left to decant (maintaining the $N_2$ atmosphere). The upper phase is separated and dried over anhydrous $Na_2SO_4$ containing 10% sodium sulfite and is finally filtered by flash silica gel, eluting with 10% hexane/THF. The fractions containing the product are pooled and rotoevaporated at 40° C., obtaining a yellow crystalline mass. The latter is dissolved in 4:1 Hexane/Cl$_2$CH$_2$ and chromatographed on silica gel, eluting with hexane/Cl$_2$CH$_2$ mixtures, starting with 4:1 and ending with pure Cl$_2$CH$_2$. The fractions containing the two isomeric adducts are pooled and rotoevaporated, obtaining 2.28 g (80% efficiency) of a white crystalline solid.

$^1$H NMR (CDCl$_3$): S Isomer (C-6): 0.07 and 0.08 (s, 12H (CH$_3$Si)), 0.66 (s, 3H (C-18), 0.87 and 0.89 (2s, 18H ((CH$_3$)$_3$C)), 1.05 (d, J: 6.6 Hz, 3H (C-21)), 3.60 and 3.94 (AB, J: 16 Hz, 2H (C-19)), 4.18 (m, 1H(C-3)), 4.37 (m, 1H (C-1)), 4.64 and 4.71 (AB, J: 10 Hz, 2H (C-6/C-7), 5.94 (d, J: 14.2 Hz (C-23)), 6.35 and 6.39 (dd, J: 14.2 Hz (C-22)) ppm.

R Isomer (C-6): It essentially has the same spectrum except that C-18 has the singlet at 0.57 ppm.

IR (KBr): 1324 and 1095 cm$^{-1}$ (SO$_2$), 1260, 837 and 724 cm$^{-1}$ (TBDMS group) and 968 cm$^{-1}$ (trans CH=CHI).

Example 2

Preparation of the Compound of Formula (IA1b)

Compound (IA1b) is obtained from the corresponding aldehyde by means of the same process of Example 1.

$^1$H NMR (CDCl$_3$): S Isomer (C-6): 0.65 (s, 3H (C-18), 1.05 (d, J: 6.6 Hz, 3H (C-21)), 2.06 and 2.08 (2s, 2×3H (COOCH$_3$)), 3.75 (qAB, J: 16 Hz, 2H (C-19)), 4.70 (m, 2H (C-6+C-7)), 5.18 (m, 1H (C-3)), 5.48 (m, 1H (C-1)), 5.94 (d, J: 14.4 Hz, 1H (C-23)), 6.35 and 6.38 (dd, J: 14.4 Hz (C-22)) ppm.

R Isomer (C-6): It essentially has the same spectrum except that C-18 has the singlet at 0.57 ppm.

IR (KBr): 1738 (CO), 1317 and 1038 cm$^{-1}$ (SO$_2$), 1236 cm$^{-1}$ (C—O), 953 cm$^{-1}$ (trans CH=CHI) cm$^{-1}$.

Example 3

Preparation of the Compound of Formula (IA2a)

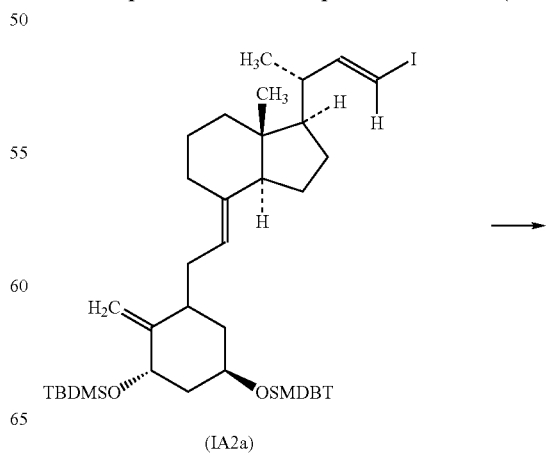

(IA1a)

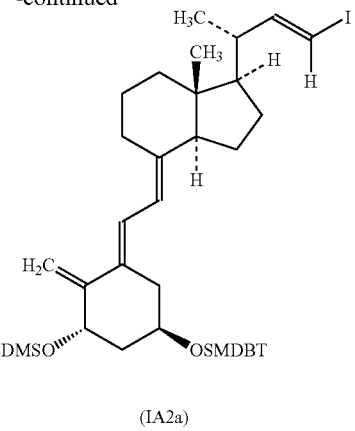

(IA2a)

3 g of compound of formula (IA1a) are added to a balloon heated at 80° C. and containing a mixture of 3 g of NaHCO$_3$ and 21 ml of DMF, and this temperature is maintained until virtually all the starting material has been consumed (usually 1.30-3 hours). Once the reaction has ended it is cooled to −10° C., the crystals are filtered and washed with cold DMF.

The crystalline mass is distributed between hexane and water, the upper phase is separated and washed with brine and sodium thiosulfate, dried and concentrated, obtaining 2.47 g (90% efficiency) of a white crystalline solid.

$^1$H NMR (CDCl$_3$): 0.061 (s, 12H(CH$_3$—Si), 0.55 (s, 3H (C-18)), 0.86 and 0.90 (2s, 18H, ((CH$_3$)$_3$C)), 1.05 (d, J: 6.8 Hz, 3H (C-21), 4.22 (m, 1H (C-3)), 4.52 (m, 1H (C-1)), 4.94 and 4.95 (dd, J=2.1 Hz, 1H (C-19)), 4.98 (d, J: 1.6 Hz, 1H ((C-19)), 5.82 (d, J: 11.48 1H (C-7)), 5.93 (d, J: 14.4 Hz, 1H (C-23)), 6.36 and 6.40 (dd, J: 14.4 Hz, 1H (C-22)), 6.45 (d, J: 11.2 Hz, 1H (C-6)) ppm.

IR (KBr): 1251, 834 and 724 cm$^{-1}$ (TBDMS groups), 1120 cm$^{-1}$ (C—O), 960 cm$^{-1}$ (trans CH=CH—I), 903 cm$^{-1}$ (C=CH$_2$).

Example 4

Preparation of the Compound of Formula (IA2b)

Compound (IA2b) is obtained from compound (IA1b) by means of the same process of Example 3.

The spectrum data are included in Example 7.

Example 5

Preparation of the Compound of Formula (IA3a)

(IA2a)

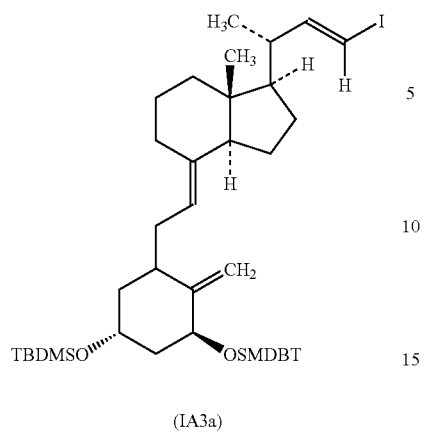

(IA3a)

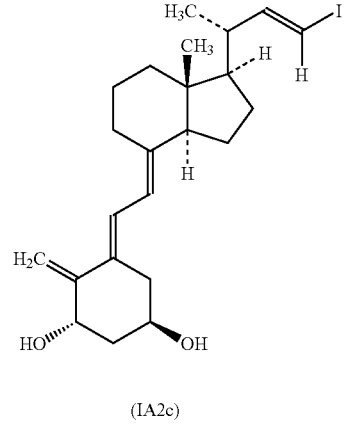

(IA2c)

A solution of 6.2 g of compound (IA2a), 1.24 g of anthracene and 100 microliters of triethylamine in 700 ml of toluene is irradiated with UV light for 45 minutes at room temperature, passing a strong $N_2$ current through the solution.

Once the reaction has ended, it is filtered, concentrated, dissolved in 50 ml of pentane and 50 ml of hexane and left at −10° C. for the anthracene to crystallize. It is filtered and concentrated, obtaining a foam which is dissolved in hexane and purified by semi-preparative chromatography, eluting with hexane/dichloromethane (6%), obtaining 3.1 g (50%) of compound (IA3a) in crystalline solid form and 1.36 g (22%) of starting compound (IA2a).

$^1$H NMR (CDCl$_3$): 0.060 (s, 12H, (CH$_3$—Si)), 0.54 (s, 3H (C-18)), 0.87 (s, 18H, ((CH$_3$)$_3$C), 1.05 (d, J: 6.8 Hz, 3H (C-21)), 4.19 (m, 1H (C-3)), 4.37 (m, 1H (C-1)), 4.86 (d, J: 2.4 Hz, 1H (C-19), 5.18 (d, J: 1.8 Hz, 1H (C-19)), 5.92 (d, J: 14.2 Hz, 1H (C-23)), 6.01 (d, J: 11.4 Hz, 1H (C-7)), 6.23 (d, J: 11.4 Hz, 1H (C-6)), 6.35 and 6.40 (dd, J: 14.2 Hz, 1H (C-22)) ppm.

IR (KBr): 1255, 1084 cm$^{-1}$ (wide band including the C—O stress), 837 and 724 cm$^{-1}$ (TBDMS groups), 960 cm$^{-1}$ (trans CH=CHI) and 908 cm$^{-1}$ (C=CH$_2$).

Example 6

Preparation of the Compound of Formula (IA2c)

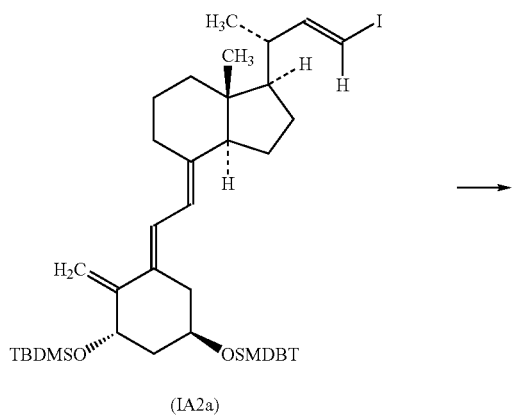

(IA2a)

A solution of 2.09 g of compound (IA2a) in 30 ml of 1 M tetrabutylammonium fluoride in THF is heated at 60° C. for 50 minutes. It is distributed between 200 ml of MTBE and 200 ml of brine and the separated organic phase is washed with 2×200 ml of sodium bicarbonate solution, dried and concentrated. The resulting crude product is purified by flash chromatography, eluting with 1:1 hexane/MTBE and then with MTBE.

The fractions containing the compound (IA2c) are pooled and concentrated, giving 1.50 g (91% efficiency) of a white solid.

$^1$H NMR (CDCl$_3$+5% CD$_3$OD): 0.57 (s, 3H (C-18)), 1.06 (d, J: 6.6 Hz, 3H (C-21)), 4.23 (m, 1H (C-3)), 4.50 (m, 1H (C-13)), 4.98 (w.b., 1H (C-19)), 5.13 (d, J: 1.5 Hz, 1H (C-19)), 5.88 (d, J: 11.4 Hz, 1H (C-7)), 5.94 (d, J: 14.2 Hz, 1H (C-23)), 6.37 and 6.40 (dd, J: 14.2 Hz, 1H (C-22)), 6.57 (d, J: 11.4 Hz, 1H (C-6)) ppm.

IR (KBr): 3600-3100 cm$^{-1}$ (OH), 1048 and 1027 cm$^{-1}$ (C—O), 950 cm$^{-1}$ (trans CH=CHI), 895 cm$^{-1}$ (C=CH$_2$).

The cis isomer (IA3c) is obtained from the corresponding cis (IA3a) by means of the same process.

$^1$H NMR (CDCl$_3$+5% CD$_3$OD): 0.55 (s, 3H (C-18)), 1.05 (d, J: 6.6 Hz, 3H (C-21)), 4.23 (m, 1H (C-3)), 4.43 (m, 1H (C-1)), 4.99 (w.b., 1H (C-19)), 5.33 (w.b., 1H (C-19)), 5.93 (d, J: 14.2 Hz, 1H (C-23)), 6.01 (d, J: 11.4 Hz, 1H (C-7)), 6.36 and 6.39 (dd, J: 14.2 Hz, 1H (C-22)), 6.37 (d, J: 11.4 Hz, 1H (C-6)) ppm.

IR (KBr): 3550-3100 cm$^{-1}$ (OH), 1060 and 1029 cm$^{-1}$ (C—O), 958 cm$^{-1}$ (trans CH=CHI), 898 cm$^{-1}$ (C=CH$_2$).

Example 7

Preparation of the Compound of Formula (IA2b)

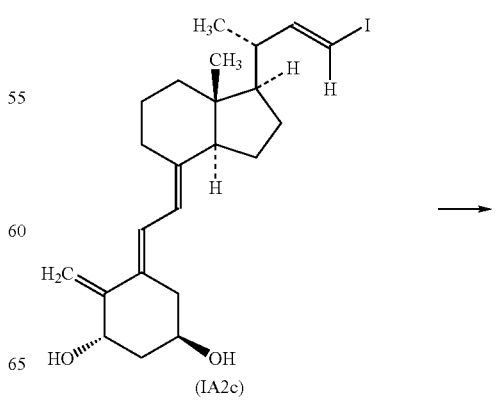

(IA2c)

-continued

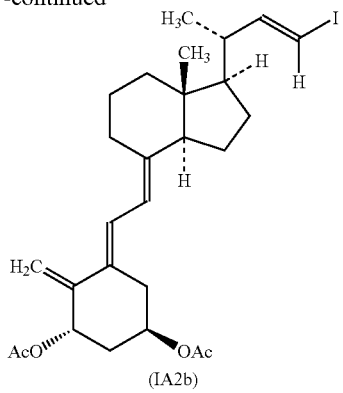

(IA2b)

2 ml of acetic anhydride are added to a mixture of 1.56 g of compound (IA2c), 0.25 g of DMAP and 2 ml of Et₃N in 25 ml of Cl₂CH₂ and is stirred for 30 minutes. It is distributed between 150 ml of MTBE and brine and the organic phase is washed with NH₄Cl solution, with diluted NH₄OH solution, and is dried and concentrated. The resulting crude product is purified by flash chromatography, eluting with mixtures of 3:1 Hexane/Cl₂CH₂ to pure Cl₂CH₂, obtaining 1.65 g (91% efficiency) of a white foam.

¹H NMR (CDCL₃): 0.55 (S, 3H (C-18)), 1.05 (D, J: 6.6 HZ, 3H (C-21)), 2.03 (S, 3H, COCH₃ (C-1)), 2.05 (S, 3H, COCH₃ (C-3)), 4.97 (S, 1H (C-19)), 5.18 (M, 1H (C-31)), 5.19 (S, 1H (C-19)), 5.56 AND 5.58 (DD, J: 5.8 HZ, 1H (C-1)), 5.81 (D, J: 11.4 HZ, 1H (C-7)), 5.94 (D, J: 14.2 HZ, 1H (C-23)), 6.36 AND 6.41 (DD, J: 14.2 HZ, 1H (C-22)), 6.54 (D, J: 11.4 HZ, 1H (C-6)) PPM.

IR (KBr): 1735 cm⁻¹ (C=O), 1233 cm⁻¹, 1025 cm⁻¹ (C—O), 955 cm⁻¹ (C=Cl), 896 cm⁻¹ (C=CH₂).

The cis isomer (IA3b) is obtained from the corresponding cis (IA3c) by means of the same process.

¹H NMR (CDCl₃): 0.52 (s, 3H (C-18)),1.05 (d, J: 6.6 Hz, 3H (C-21)), 2.05 (s, 3H, COCH₃ (C-1)), 2.06 (s, 3H, COCH₃ (C-3)), 5.03 (w.b., 1H (C-19)), 5.18 (m, 1H (C-3)), 5.30 (w.b., 1H (C-19)), 5.46 (m, 1H (C-1)), 5.91 (d, J: 14.2 Hz, 1H (C-23)), 5.96 (d, J: 11.4 Hz, 1H (C-7)), 6.35 (d, J: 11.4 Hz, 1H (C-6)), 6.36 and 6.40 (dd, J: 14.2 Hz, 1H (C-22)) ppm IR (KBr): 1735 cm⁻¹ (C=O), 1233 cm⁻¹ and 1025 cm⁻¹ (C—O), 957 cm⁻¹ (trans CH=CHI), 897 cm⁻¹ (C=CH₂).

Example 8

Preparation of the Compound of Formula (IA1c)

3.0 g of compound (IA2c) dissolved in 3 ml of Cl₂CH₂ and 0.5 ml of ethanol are added to 10 ml of liquid SO₂ at a temperature of −20° C. The temperature is left to increase up to −10° C. and is maintained at this temperature for one hour. The SO₂ and the solvents are distilled and compound (IA2c) is obtained in the form of a yellowish-white foam.

¹H NMR (CDCl₃+5% CD₃OD): S Isomer (C-6): 0.65 (s, 3H (C-18), 1.06 (d, J: 6.6 Hz, 3H (C-21)), 3.86 (qAB, J: 15.6 Hz, 2H (C-19)), 4.22 (m, 1H (C-3)), 4.38 (m, 1H (C-1)), 4.70 (qAB, J: 10.2 Hz, 2H (C-6+C-7)), 5.94 (d, J: 14.4 Hz, 1H (C-23), 6.36 and 6.39 (dd, J: 14.4 Hz (C-22)) ppm.

R Isomer (C-6): It essentially has the same spectrum except that C-18 has the singlet at 0.57 ppm.

IR (KBr): 3700-3000 (OH), 1305 and 1055 cm⁻¹ (SO₂), 1113 cm⁻¹ (C—O), 957 cm⁻¹ (trans CH=CHI) cm⁻¹.

Example 9

Preparation of the Compounds of Formula (IA2a) and (IA3a)

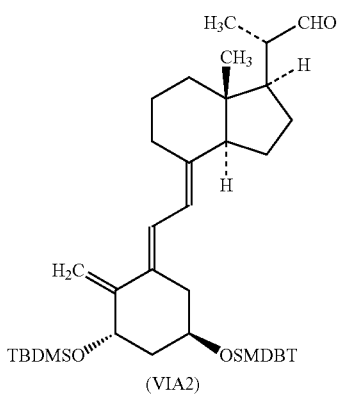

(VIA2)

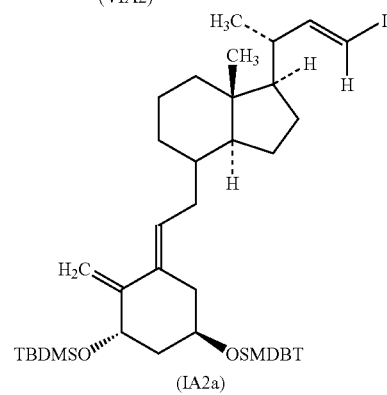

(IA2a)

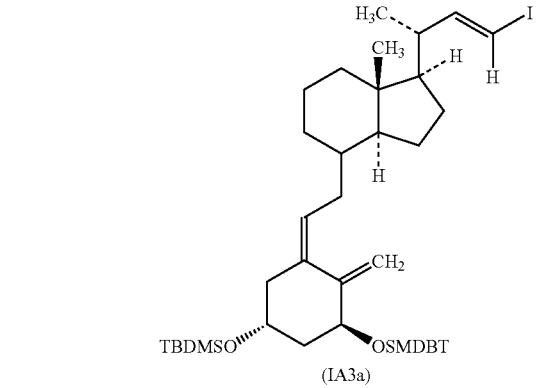

(IA3a)

(R₁, R₃ = H; Z, Z' = TBDMSO⁻)

A solution of 2.30 g of aldehyde (VIA2) and 3.14 g of iodoform in 10 ml of anhydrous THF is added dropwise to a suspension of 3.0 g of chromium chloride in 20 ml of anhydrous THF cooled at 0° C. When the aldehyde has disappeared (TLC, 95:5 hexane/diethyl ether, usually 2-3 hours) NH₄Cl is added and it is extracted with hexane. It is dried and concentrated to dryness, and the resulting crude product is purified by flash chromatography, eluting with increasing mixtures of hexane/Cl₂CH₂ (from 2% to 50%).

2.08 g (75% efficiency) of an approximately mixture 2:1 of trans/cis iodine derivatives are obtained.

The mixture is dissolved in hexane and purified by semi-preparative chromatography, eluting with hexane/dichloromethane (6%), obtaining 0.62 g of compound (IA3a) and 1.41 g of compound (IA2a).

The invention claimed is:
1. A compound of formula (I)

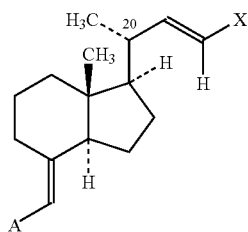

wherein:
X represents a halogen atom selected from chlorine, bromine and iodine and
A is selected from any of the moieties corresponding to formulas (A2) and (A3)

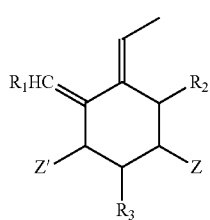

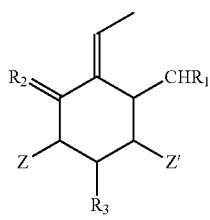

in which:
Z and Z' are independently selected from hydrogen, a hydroxyl group and an —OR protected hydroxyl group, where R is a hydroxyl protective group; and
R1, R2 and R3 are independently selected from hydrogen, halogen, a hydroxyl group, C1-C6 alkyl or C1-C6 alkenyl, optionally substituted with halogen, hydroxyl, cyano or amino, or a dialkyl(C1-C5)ether or alkyl(C1-C5)amino group, and an —OR protected hydroxyl group wherein R is a hydroxyl protective group.

2. A compound according to claim 1, wherein X is an iodine atom.

3. A compound according to claim 1, wherein R1, R2 and R3 are independently selected from hydrogen, halogen and hydroxyl.

4. A compound according to claim 3, wherein R1, R2 and R3 are simultaneously hydrogen.

5. A compound according to claim 1, wherein Z and Z' are independently selected from a hydroxyl group and an —OR protected hydroxyl group in which the protective group is selected from a silyl ether and a carboxylic ester.

6. A compound according to claim 1, selected from the group formed by:

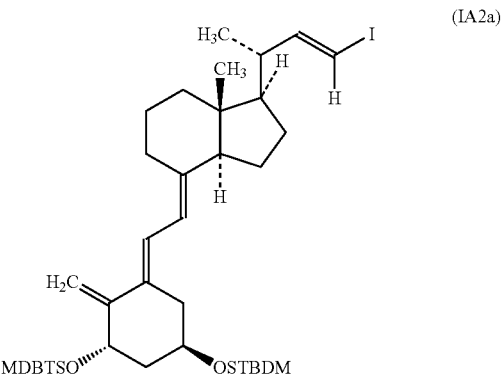

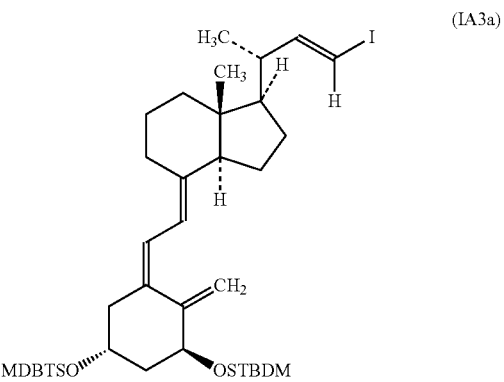

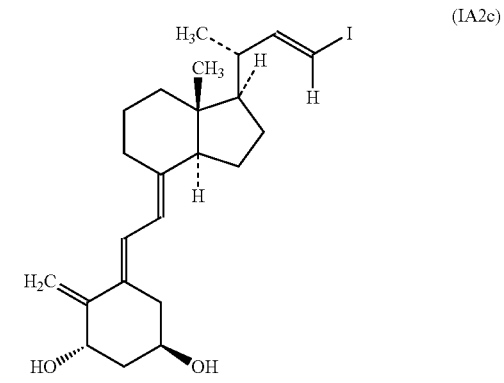

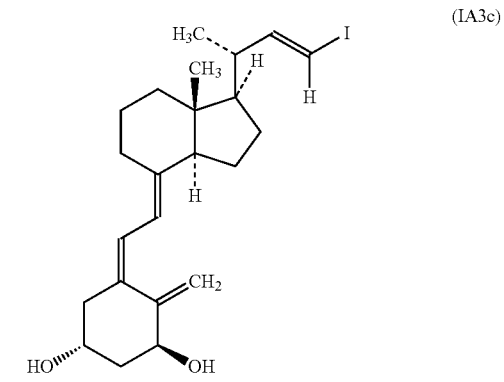

-continued

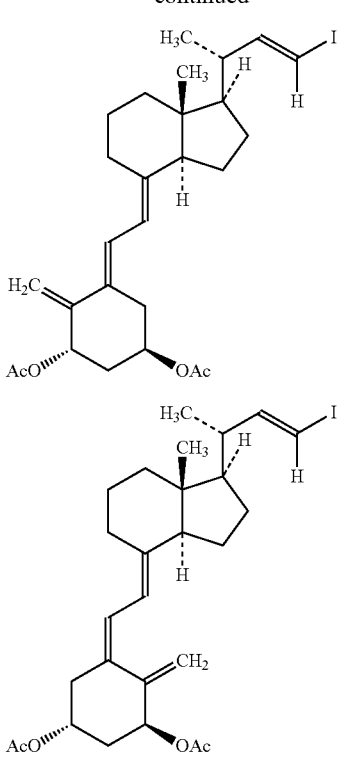

where
STBDM or MDBTS represents a t-butyldimethylsilyl group; and
OAc or AcO represent an acetoxy group.

7. A process for preparing a compound of formula (I) according to claim 1, comprising reacting an aldehyde of formula (VI)

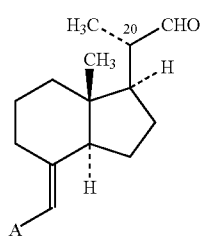

wherein A has the meaning indicated in relation to the compounds of formula (I), with a haloform selected from chloroform, bromoform and iodoform, in the presence of a divalent chromium (Cr2+) salt or complex.

8. A process according to claim 7, wherein the reaction of the aldehyde with the haloform is carried out in a polar aprotic solvent.

9. A process according to claim 8, wherein said polar aprotic solvent is an ether.

10. A process according to claim 9, wherein said polar aprotic solvent is tetrahydrofuran (THF).

11. A process according to claim 7, wherein the reaction of the aldehyde with the haloform is carried out at a temperature comprised between −50° C. and +30° C.

12. A process according to claim 7, wherein said divalent chromium salt is Cr2+ chloride (Cl2Cr).

13. A process according to claim 7, wherein the divalent chromium can be regenerated with manganese/trichloromethylsilane.

14. A process according to claim 7, wherein the divalent chromium is obtained in situ from a trivalent chromium salt by means of reaction with a metal hydride or with tetrakis (dimethylaminoethylene), or by electroreduction, or by metal manganese.

15. A process according to claim 7, comprising converting the obtained compound of formula (I) into another compound of formula (I), such that when
moiety A in the starting aldehyde (VI) corresponds to formula (A2) and the compound of formula (I) is wished to be obtained in which A is the moiety of formula (A3), the product obtained from the reaction of the aldehyde with the haloform in the presence of a Cr2+ complex or salt is subjected to UV or VIS light irradiation until obtaining the 5(Z) configuration.

16. A process according to claim 15, wherein when a moiety of formula (A2) is to be converted into a moiety of formula (A3), light irradiation is carried out in the presence of iodine or diphenyl selenide and diffuse light, or else in the presence of photosensitizers derived from anthracene, acridine or phenazine and ultraviolet light.

17. A process according to claim 15, wherein the compounds of formula (I) in which Z and/or Z' are free hydroxyl groups are obtained by means of deprotection of the corresponding compounds in which Z and Z' are (—OR) protected hydroxyl groups.

18. A process according to claim 15, wherein the compounds of formula (I) in which Z and/or Z' are (—OR) protected hydroxyl groups are obtained by means of the protection of the corresponding compounds in which Z and Z' are free hydroxyl groups.

19. A compound according to claim 1, wherein formula (I) is obtained from formula (VI) by reacting said compound of formula (VI) with a haloform selected from chloroform, bromoform and iodoform, in the presence of a divalent chromium ($Cr^{2+}$) salt or complex

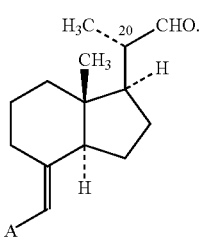

20. A compound according to claim 1, wherein A is selected from any of the moieties corresponding to formulas (A2) and (A3).

21. A compound according to claim 1, wherein R is a hydroxyl protective group selected from silyl-ethers and esters.

* * * * *

UNITED STATES PATENT AND TRADEMARK OFFICE
CERTIFICATE OF CORRECTION

PATENT NO.        : 7,906,495 B2
APPLICATION NO.   : 10/579594
DATED             : March 15, 2011
INVENTOR(S)       : Antonio Buxadé Viñas et al.

It is certified that error appears in the above-identified patent and that said Letters Patent is hereby corrected as shown below:

Claim 1, column 17, delete the figure (A3), line 37-45

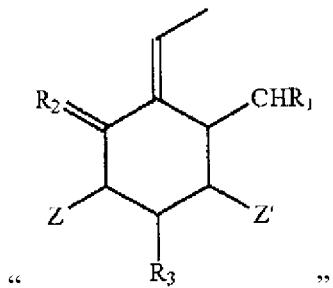

and substitute therefor:

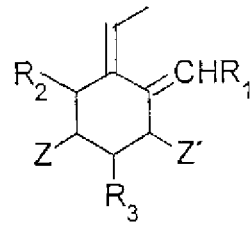

Signed and Sealed this
Seventeenth Day of May, 2011

David J. Kappos
*Director of the United States Patent and Trademark Office*